United States Patent
Bhirud et al.

(10) Patent No.: US 11,447,448 B2
(45) Date of Patent: Sep. 20, 2022

(54) PROCESS FOR THE PREPARATION OF SOLRIAMFETOL AND SALT THEREOF

(71) Applicant: Glenmark Life Sciences Limited, Solapur (IN)

(72) Inventors: Shekhar Bhaskar Bhirud, Mumbai (IN); Samir Naik, Jr., Thane (IN); Sushanta K. Mishra, Bolangir (IN); Rahul Bhalchadrarao Kawthekar, Palava Dombivali (IN); Deepak Shantaram Patekar, Navi Mumbai (IN); Nitesh Patil, Rasayani (IN)

(73) Assignee: Glenmark Life Sciences Limited, Solapur (IN)

(*) Notice: Subject to any disclaimer, the term of this patent is extended or adjusted under 35 U.S.C. 154(b) by 0 days.

(21) Appl. No.: 17/265,356

(22) PCT Filed: Aug. 9, 2019

(86) PCT No.: PCT/IB2019/056791
§ 371 (c)(1),
(2) Date: Feb. 2, 2021

(87) PCT Pub. No.: WO2020/035769
PCT Pub. Date: Feb. 20, 2020

(65) Prior Publication Data
US 2022/0162159 A1    May 26, 2022

(30) Foreign Application Priority Data
Aug. 14, 2018 (IN) .............................. 201821030526

(51) Int. Cl.
*C07C 269/06* (2006.01)
*C07C 271/12* (2006.01)

(52) U.S. Cl.
CPC .......... *C07C 269/06* (2013.01); *C07C 271/12* (2013.01)

(58) Field of Classification Search
None
See application file for complete search history.

(56) References Cited

U.S. PATENT DOCUMENTS

| | | | |
|---|---|---|---|
| 5,756,817 A * | 5/1998 | Choi | C07C 271/12 560/115 |
| 5,955,499 A | 9/1999 | Choi et al. | |
| 2005/0080268 A1 * | 4/2005 | Choi | C07C 269/00 546/233 |

FOREIGN PATENT DOCUMENTS

| | | | | |
|---|---|---|---|---|
| WO | WO-2013072933 A2 * | 5/2013 | ........... | C07C 231/02 |
| WO | 2018048871 A1 | 3/2018 | | |

* cited by examiner

*Primary Examiner* — Amy C Bonaparte
(74) *Attorney, Agent, or Firm* — Ryan, Mason & Lewis, LLP (57) ABSTRACT

The present invention relates to solriamfetol or novel salts thereof and its process for preparation. More particularly the present invention relates to solriamfetol dibenzoyl-D-tartaric acid salt or solriamfetol di-p-toluoyl-D-tartaric acid salt and their process for preparation. Further the present invention relates to use of solriamfetol dibenzoyl-D-tartaric acid salt or solriamfetol di-p-toluoyl-D-tartaric acid salt for the preparation of solriamfetol hydrochloride.

10 Claims, 4 Drawing Sheets

PROCESS FOR THE PREPARATION OF SOLRIAMFETOL AND SALT THEREOF

PRIORITY

This application claims priority under 35 U.S.C. § 371 to International Application No. PCT/M2019/056791, filed Aug. 9, 2019, which claims the benefit of Indian Provisional Application No. 201821030526, filed Aug. 14, 2018, entitled "PROCESS FOR THE PREPARATION OF SOLRIAMFETAL AND SALT THEREOF", the contents of each of which are incorporated herein by reference.

FIELD OF THE INVENTION

The present invention relates to solriamfetol or salt thereof and its process for preparation.

BACKGROUND OF THE INVENTION

Solriamfetol hydrochloride, chemically known as (R)-2-amino-3-phenylpropylcarbamate hydrochloride, is represented by compound of formula Ia.

Formula Ia

Solriamfetol, a dopamine and norepinephrine reuptake inhibitor (DNRI), is marketed in the United States under the trade name SUNOSI® as tablets in the dosage strength of 75 mg and 150 mg.

Solriamfetol hydrochloride can be used to improve wakefulness in adult patients with excessive daytime sleepiness associated with narcolepsy or obstructive sleep apnea (OSA).

U.S. Pat. No. 5,955,499 discloses a process for the preparation of solriamfetol hydrochloride There is a need for an improved process for the preparation of solriamfetol, which avoids the formation of isomeric and other process-related impurities, while affording the desired solriamfetol hydrochloride product with good yield and high purity.

The present invention provides a process for solriamfetol HCl in a high chemical and chiral purity by using novel acid addition salts of solriamfetol without using chromatographic techniques.

SUMMARY OF THE INVENTION

The present invention provides, a process for the preparation of R-solriamfetol HCl of formula Ia,

Formula Ia the process comprising:
(a) reacting solriamfetol of formula I, Formula I with an acid to form solriamfetol acid addition salt of formula II;

Formula II (b) optionally purifying the solriamfetol acid addition salt of formula II;
(c) converting the solriamfetol acid addition salt of formula II to solriamfetol HCl of formula Ia; and
(d) optionally purifying the solriamfetol hydrochloride of formula Ia.

The present invention provides solriamfetol dibenzoyl-D-tartaric acid salt of formula IIa characterized by $^1$H NMR having peaks at 2.65-2.71, 2.88, 3.39, 3.72-3.86, 5.69, 6.61, 7.16-7.25, 7.44-7.48, 7.60-8.00 (400 MHz, DMSO $d_6$).

The present invention provides, a process for solriamfetol dibenzoyl-D-tartaric acid salt of formula IIa, comprising reacting solriamfetol of formula I with dibenzoyl-D-tartaric acid.

DETAILED DESCRIPTION OF THE INVENTION

The present invention provides a process for the preparation of R-solriamfetol HCl of formula Ia,

Formula Ia the process comprising:
(a) reacting solriamfetol of formula I, Formula I with an acid to form solriamfetol acid addition salt of formula II;

Formula II (b) optionally purifying the solriamfetol acid addition salt of formula II;
(c) converting the solriamfetol acid addition salt of formula II to solriamfetol HCl of formula Ia; and
(d) optionally purifying the solriamfetol hydrochloride of formula Ia.

In one embodiment, the present invention provides R-solriamfetol HCl of formula Ia having chemical purity of at least 98% as determined by HPLC.

The acid used in step (a) may be selected from the group consisting of an organic acid and an optically active acid.

The organic acid may be selected from the group consisting of formic acid, acetic acid, citric acid, tartaric acid, bitartaric acid, benzoic acid, lactic acid, oxalic acid, malic acid, fumaric acid, succinic acid, gluconic acid, pamoic acid, methanesulfonic acid, benzenesulfonic acid.

The optically active acid may be selected from the group consisting of (+)-dibenzoyl-D-tartaric acid, (−)-dibenzoyl-L-tartaric acid, (+)-di-p-toluoyl-D-tartaric acid, (−)-di-p-toluoyl-L-tartaric acid, S-(+) mandelic acid, R-(−) mandelic acid, L-(+) tartaric acid, D-(−) tartaric acid, L-malic acid, D-malic acid, D-maleic acid, (1R)-(−)-camphor sulfonic acid, (1S)-(+)-camphor sulfonic acid, L-(−)-pyroglutamic acid, L-(+)-pyroglutamic acid, (−)-lactic acid.

In one embodiment, in optically active acid is dibenzoyl-D-tartaric acid and di-p-toluoyl-D-tartaric acid.

In one embodiment, in step (a) reaction is carried out in presence of solvent which includes but is not limited to hydrocarbons such as methylene dichloride, ethylene dichloride, chloroform, carbon tetrachloride, toluene, xylene, heptane, hexane, cyclohexane and the like; esters such as methyl acetate, ethyl acetate, n-propyl acetate, isopropyl acetate, butyl acetate, tert-butyl acetate and the like; alcohols such as methanol, ethanol, isopropanol, n-propanol, butanol and the like; ethers such as diethyl ether, diisopropyl ether, methyl tert-butyl ether, tetrahydrofuran and the like; ketones such as acetone, ethyl methyl ketone, methyl isobutyl ketone and the like; water and or mixtures thereof.

In step (b) the acid addition salt of compound of formula II is purified by a solvent selected from but not limited to alcohols such as methanol, ethanol, isopropanol, n-propanol, butanol and the like; ketones such as acetone, ethyl methyl ketone, methyl isobutyl ketone and the like; ethers such as diethyl ether, diisopropyl ether, methyl tert-butyl ether, tetrahydrofuran and the like; esters such as methyl acetate, ethyl acetate, n-propyl acetate, isopropyl acetate, butyl acetate, tert-butyl acetate and the like; water and or mixtures thereof.

In one embodiment, solriamfetol acid addition salt of formula II obtained in step (b) is filtered and dried.

In one embodiment, solriamfetol acid addition salt of formula II is isolated by filtration, centrifugation or by a method known in the art.

In one embodiment, drying may be performed under vacuum at a temperature of about 50-70° C., preferably at a temperature of 50-60° C.

In step (c) solriamfetol acid addition salt of formula II is treated with HCl in an organic solvent to form solriamfetol HCl of formula Ia.

The organic solvent used in step (c) includes, but is not limited to esters such as methyl acetate, ethyl acetate, n-propyl acetate, isopropyl acetate, butyl acetate, tert-butyl acetate and the like; ethers such as diethyl ether, diisopropyl ether, methyl tert-butyl ether, tetrahydrofuran and the like; ketones such as acetone, ethyl methyl ketone, methyl isobutyl ketone and the like; alcohols such as methanol, ethanol, isopropanol, n-propanol, butanol and the like; mixtures thereof. In one embodiment, in step (c) solriamfetol acid addition salt of formula II is treated with HCl source in an organic solvent to directly obtain solriamfetol HCl of formula Ia.

In one embodiment, in step (c) solriamfetol acid addition salt of formula II is treated with HCl source in an organic solvent to directly obtain solriamfetol HCl of formula Ia, without isolating solriamfetol free base.

In one embodiment, in step (c) solriamfetol acid addition salt of formula II is treated with HCl in non-aqueous medium.

The addition of hydrochloric acid may be by purging dry HCl gas or by addition of hydrochloric acid dissolved in an organic solvent.

In one embodiment, solriamfetol HCl of formula Ia obtained in step (c) is filtered and dried.

In step (d) R-solriamfetol HCl of formula Ia may be purified from a suitable solvent selected from alcohols such as methanol, ethanol, propanol, isopropanol and the like; esters such as ethyl acetate, isopropyl acetate and the like; ketone such as acetone, methyl ethyl ketone, methyl isobutyl ketone and the like; ethers such as diethyl ether, diisopropyl ether, methyl tert-butyl ether, tetrahydrofuran and the like or mixtures thereof.

In one embodiment, solriamfetol HCl of formula Ia is isolated by filtration, centrifugation or by a method known in the art.

In one embodiment, drying may be performed under vacuum at a temperature of about 50-70° C., preferably at a temperature of 50-60° C.

In one embodiment, the present invention provides a process for the preparation of R-solriamfetol HCl of formula Ia,

Formula Ia the process comprising: (a) reacting solriamfetol of formula I, Formula I with an optically active acid to form solriamfetol acid addition salt of formula II;

Formula II

·acid addition salt (b) optionally purifying the solriamfetol acid addition salt of formula II;

(c) converting the solriamfetol acid addition salt of formula II to solriamfetol HCl of formula Ia.

In step (a) an optically active acid is selected from the group consisting of (+)-dibenzoyl-D-tartaric acid, (−)-dibenzoyl-L-tartaric acid, (+)-di-p-toluoyl-D-tartaric acid, (−)-di-p-toluoyl-L-tartaric acid.

In step (c) solriamfetol acid addition salt of formula II is treated with HCl source in an organic solvent to form solriamfetol HCl of formula Ia.

The hydrochloride source is selected from but not limited to hydrochloride gas, concentrated hydrochloric acid, ethyl acetate-hydrochloride, ethanol-hydrochloride, isopropanol-hydrochloride and the like.

The organic solvent used is as described supra.

In one embodiment, the present invention provides a process for the preparation of R-solriamfetol HCl of formula Ia,

Formula Ia

·HCl the process comprising:
(a) reacting solriamfetol of formula I,
with (+)-dibenzoyl-D-tartaric acid to form solriamfetol dibenzoyl-D-tartaric acid of formula IIa;

Formula IIa

-continued (b) optionally purifying the solriamfetol dibenzoyl-D-tartaric acid of formula IIa;

(c) converting the solriamfetol dibenzoyl-D-tartaric acid of formula IIa to solriamfetol HCl of formula Ia; and (d) optionally purifying the solriamfetol hydrochloride of formula Ia.

In step (b) solriamfetol dibenzoyl-D-tartaric acid of formula IIa is purified from methanol, ethanol, isopropanol or aqueous mixture thereof.

In step (c) solriamfetol dibenzoyl-D-tartaric acid of formula IIa is treated with HCl source in an organic solvent to form solriamfetol HCl of formula Ia.

The hydrochloride source used is as described supra. The organic solvent used is as described supra.

In step (d) R-solriamfetol HCl of formula Ia is purified or recrystallized from a suitable solvent as described supra.

In one embodiment, the present invention provides R-solriamfetol HCl of formula Ia having chemical purity of at least 99% as determined by HPLC.

In one embodiment, the present invention provides R-solriamfetol HCl of formula Ia having chemical purity greater than 99.5% as determined by HPLC.

In one embodiment, the present invention provides R-solriamfetol HCl of formula Ia having chemical purity greater than 99.8% as determined by HPLC.

In one embodiment, the present invention provides R-solriamfetol HCl of formula Ia having chemical purity in the range of 99% to 99.98% as determined by HPLC.

In one embodiment, the present invention provides R-solriamfetol HCl of formula Ia having chiral purity greater than 99% as determined by HPLC.

In one embodiment, the present invention provides R-solriamfetol HCl of formula Ia having chiral purity greater than 99.5% as determined by HPLC.

In one embodiment, the present invention provides R-solriamfetol HCl of formula Ia having chiral purity greater than 99.8% as determined by HPLC.

In one embodiment, the present invention provides R-solriamfetol HCl with a chemical purity of at least 99% and a chiral purity of at least 99% as determined by HPLC.

In one embodiment, the present invention provides R-solriamfetol HCl of formula Ia free of other isomer i.e. S-solriamfetol.

In one embodiment, the present invention provides R-solriamfetol HCl of formula Ia having chiral purity of 100% as determined by HPLC.

In one embodiment, the present invention provides solriamfetol hydrochloride, where is one or more of impurity A, impurity B, impurity C, impurity D, impurity E, impurity F, impurity G, impurity H or impurity I are present less than 0.15% w/w relative to the amount of R-solriamfetol as determined by HPLC.

| Impurity | Structure | Chemical Name |
| --- | --- | --- |
| A | | 1-[(2R)-1-hydroxy-3-phenylpropan-2-yl]urea |
| B | | (2R)-2-(carbamoylamino)-3-phenylpropyl carbamate |
| C | | Methyl (2R)-2-(carbamoylamino)-3-phenyl propanoate |
| D | | (2R)-2-amino-3-phenyl propyl hydrogen carbonate |
| E | | 2-amino-N-(1-hydroxy-3-phenylpropan-2-yl)-3-phenylpropanamide |
| F | | (2R)-2-{[(2R)-2-amino-3-phenylpropanoyl]amino}-3-phenylpropyl carbamate |
| G | | N-[(2R)-1-hydroxy-3-phenylpropan-2-yl]dicarbonimidic diamide |
| H | | (2R)-2-amino-3-phenylpropyl carbamoyl carbamate |

| Impurity | Structure | Chemical Name |
|---|---|---|
| I | | (2R)-2-(carbamoylamino)-3-phenylpropylcarbamoyl carbamate |

In one embodiment, the present invention provides solriamfetol hydrochloride of formula Ia, wherein impurity B, impurity F or impurity G are present less than 0.15% w/w relative to the amount of R-solriamfetol as determined by HPLC.

HPLC Methodology

Reagents and Solvents:

Water (Milli Q or equivalent); Acetonitrile (Gradient Grade, Rankem)

Perchloric acid 70% (AR grade, Rankem)

Chromatographic Conditions:

Apparatus: A High Performance Liquid Chromatograph equipped with quaternary gradient pumps, variable wavelength UV detector attached with data recorder and integrator software.

Column: Inertsil ODS HL, 250×4.6 mm, 5μ

Column temperature: 40° C.

Mobile Phase: Mobile Phase A=Buffer (100%)

Buffer: 0.1% Perchloric acid in water

Mobile Phase B=Acetonitrile:Buffer (90:10, v/v)

| Time (min.) | % Mobile Phase A | % Mobile Phase B |
|---|---|---|
| 0.01 | 90 | 10 |
| 14 | 83 | 17 |
| 40 | 65 | 35 |
| 70 | 35 | 65 |
| 85 | 35 | 65 |
| 87 | 90 | 10 |
| 95 | 90 | 10 |

Diluent: Water:Acetonitrile (80:20, v/v)

Flow Rate: 1.0 mL/min

Detection: UV 210 nm

Injection Volume: 20 μL

The retention time of main peak of solriamfetol hydrochloride is about 14.0 minutes under these conditions.

In one embodiment, the present invention provides solriamfetol dibenzoyl-D-tartaric acid salt of formula IIa, In one embodiment, the present invention provides solriamfetol dibenzoyl-D-tartaric acid salt of formula IIa characterized by $^1$H NMR having peaks at 2.65-2.71, 2.88, 3.39, 3.72-3.86, 5.69, 6.61, 7.16-7.25, 7.44-7.48, 7.60-8.00 (400 MHz, DMSO $d_6$).

Figure 3:
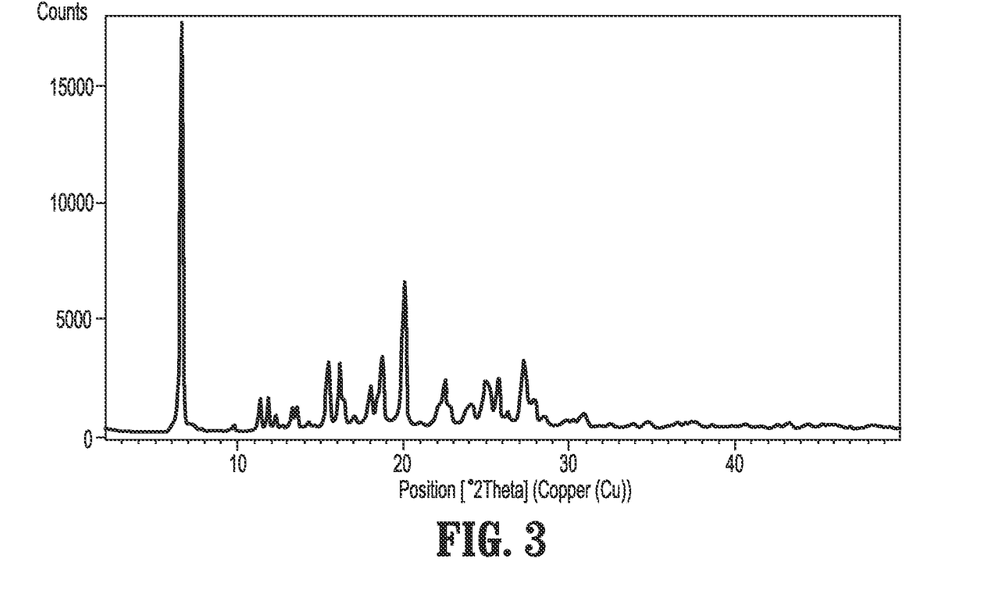
FIG. 3 is a characteristic XRPD of solriamfetol dibenzoyl-D-tartaric acid as obtained in Example 17.

In one embodiment, the present invention provides a crystalline solriamfetol dibenzoyl-D-tartaric acid salt of formula IIa characterized by an X-ray powder diffraction spectrum having peak reflections at about 6.68, 15.53, 16.22, 18.73 and 20.12±0.2 degrees 2 theta which is substantially in accordance with FIG. 3.

Figure 4:
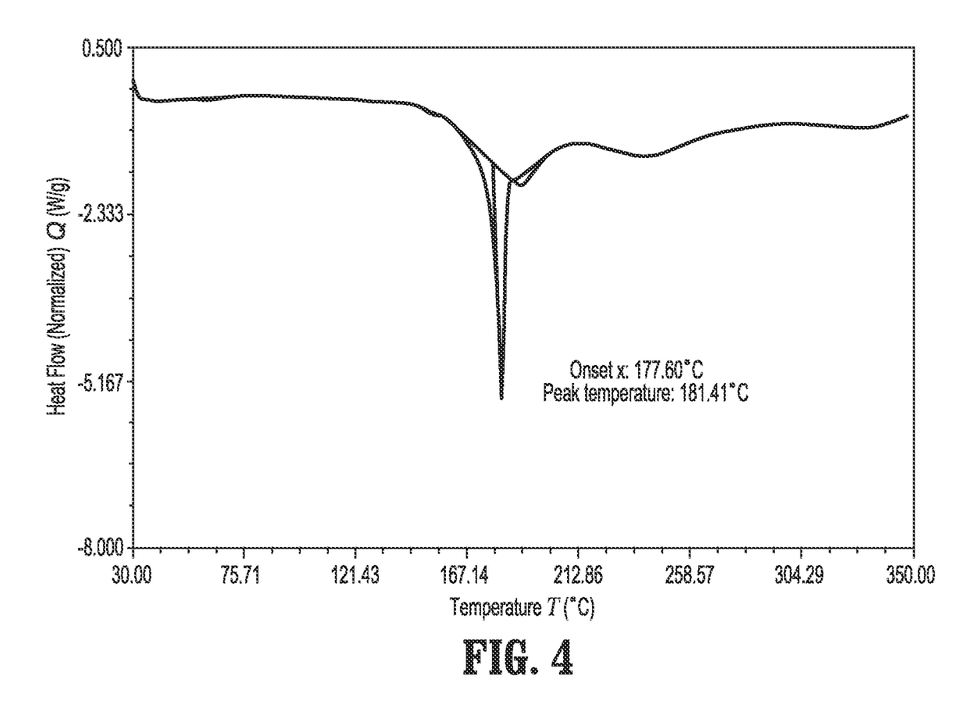
FIG. 4 is a DSC thermogram of solriamfetol dibenzoyl-D-tartaric acid as obtained in Example 17.

In one embodiment, the present invention provides a crystalline solriamfetol dibenzoyl-D-tartaric acid salt of formula IIa characterized by DSC thermogram having endothermic peak at about 177.60° C. and 181.41° C.±2° C. which is substantially in accordance with FIG. 4.

In one embodiment, present invention provides crystalline solriamfetol dibenzoyl-D-tartaric acid salt of formula IIa characterized by TGA thermogram, showing weight loss of about less than 0.5 weight % up to 100° C. determined over the temperature range of 0° C. to 350° C. and heating rate 10° C./min.

In one embodiment, the present invention provides, a process for solriamfetol dibenzoyl-D-tartaric acid salt of formula IIa, comprising reacting solriamfetol of formula I with dibenzoyl-D-tartaric acid.

In one embodiment, the present invention provides solriamfetol dibenzoyl-L-tartaric acid salt of formula IIb,

Formula IIa

Formula IIb

-continued

In one embodiment, the present invention provides a process for dibenzoyl-L-tartaric acid salt of solriamfetol of formula IIb, comprising reacting solriamfetol of formula I with dibenzoyl-L-tartaric acid.

In one embodiment, the purification or recrystallization of dibenzoyl-D-tartaric acid or dibenzoyl-L-tartaric salt of solriamfetol of formula IIa or IIb may be carried out in a suitable solvent selected from alcohols such as methanol, ethanol, propanol, isopropanol and the like; esters such as ethyl acetate, isopropyl acetate and the like; ketone such as acetone, methyl ethyl ketone, methyl isobutyl ketone and the like; ethers such as diethyl ether, diisopropyl ether, methyl tert-butyl ether, tetrahydrofuran and the like; water or mixtures thereof.

In one embodiment, the present invention provides crystalline solriamfetol dibenzoyl-D-tartaric acid salt of formula IIa.

In one embodiment, the present invention provides crystalline solriamfetol dibenzoyl-D-tartaric acid salt of formula IIa having chemical purity of at least 98% as determined by HPLC.

In one embodiment, the present invention provides crystalline solriamfetol dibenzoyl-D-tartaric acid salt of formula IIa having chiral purity greater than 99% as determined by HPLC.

In one embodiment, the present invention provides solriamfetol di-p-toluoyl-D-tartaric acid salt of formula IIc, Formula IIc In one embodiment, the present invention provides solriamfetol di-p-toluoyl-D-tartaric acid salt of formula IIc characterized by $^1$H NMR having peaks at 2.34, 2.70-2.76, 2.88-2.93, 3.48-3.51, 3.72-3.86, 5.60, 6.61, 7.16-7.31, 7.84-7.86 (400 MHz, DMSO d$_6$).

Figure 1:
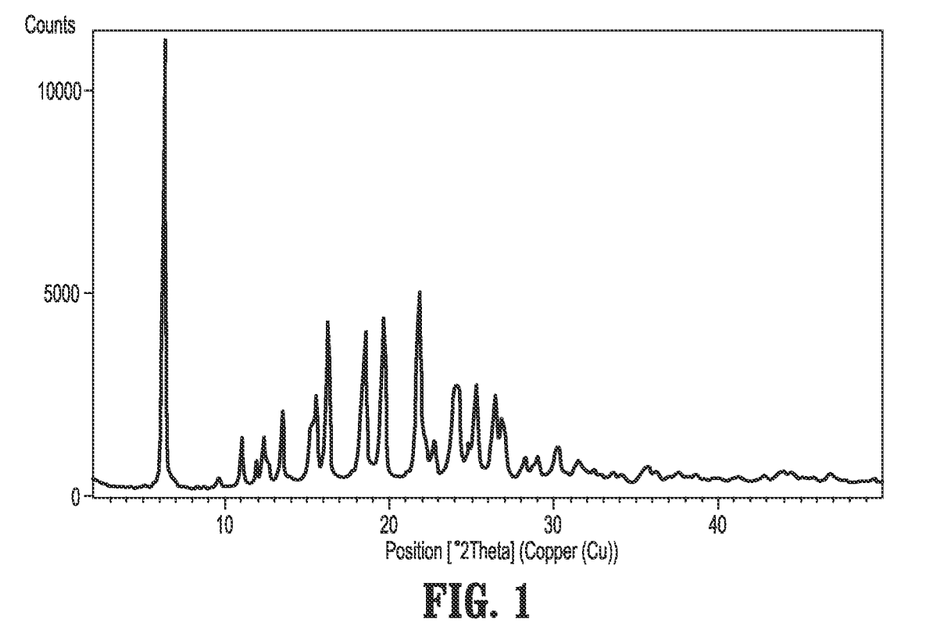
FIG. 1 is a characteristic XRPD of solriamfetol di-p-toluoyl-D-tartaric acid as obtained in Example 8.

In one embodiment, the present invention provides a crystalline solriamfetol di-p-toluoyl-D-tartaric acid salt of formula IIc characterized by an X-ray powder diffraction spectrum having peak reflections at about 6.33, 16.32, 18.55, 19.65 and 21.85±0.2 degrees 2 theta which is substantially in accordance with FIG. 1.

Figure 2:
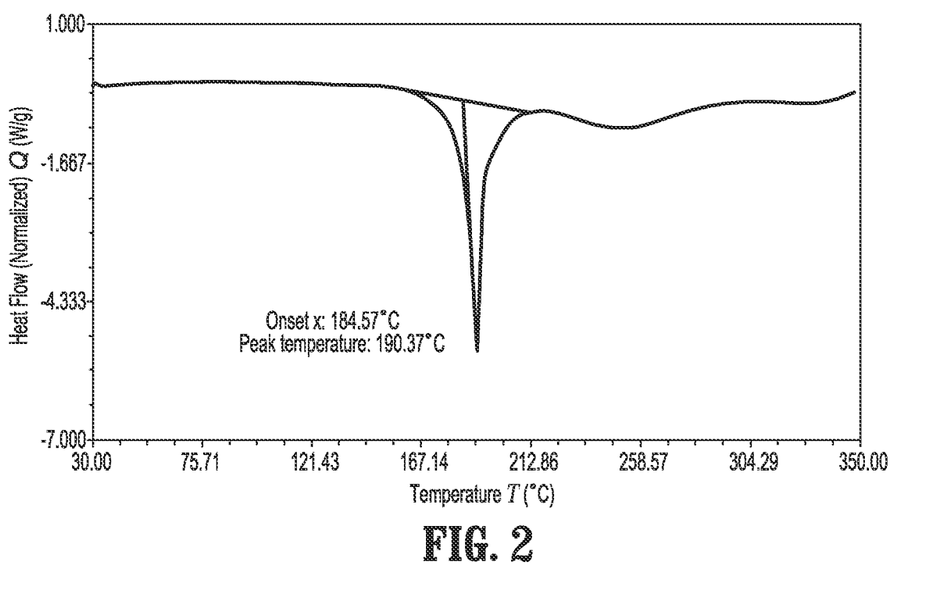
FIG. 2 is a DSC thermogram of solriamfetol di-p-toluoyl-D-tartaric acid as obtained in Example 8.

In one embodiment, the present invention provides a crystalline solriamfetol di-p-toluoyl-D-tartaric acid salt of formula IIc characterized by DSC thermogram having endothermic peak at about 184.57° C. and 190.37° C.±2° C. which is substantially in accordance with FIG. 2.

In one embodiment, present invention provides crystalline solriamfetol di-p-toluoyl-D-tartaric acid salt of formula IIc characterized by TGA thermogram, showing weight loss of about less than 1.0 weight % up to 100° C. determined over the temperature range of 0° C. to 350° C. and heating rate 10° C./min.

In one embodiment, the present invention provides a process for di-p-toluoyl-D-tartaric acid salt of solriamfetol of formula IIc, comprising reacting solriamfetol of formula I with di-p-toluoyl-D-tartaric acid.

In one embodiment, the present invention provides di-p-toluoyl-L-tartaric acid salt of solriamfetol of formula IId, Formula IId In one embodiment, the present invention provides a process for di-p-toluoyl-L-tartaric acid salt of solriamfetol of formula IId, comprising reacting solriamfetol, a compound of formula I with di-p-toluoyl-L-tartaric acid.

In one embodiment, the purification or recrystallization of D or L di-p-toluoyl-tartaric acid salt of solriamfetol of formula IIc or IId may be carried out in a suitable solvent as described supra.

Figure 5:
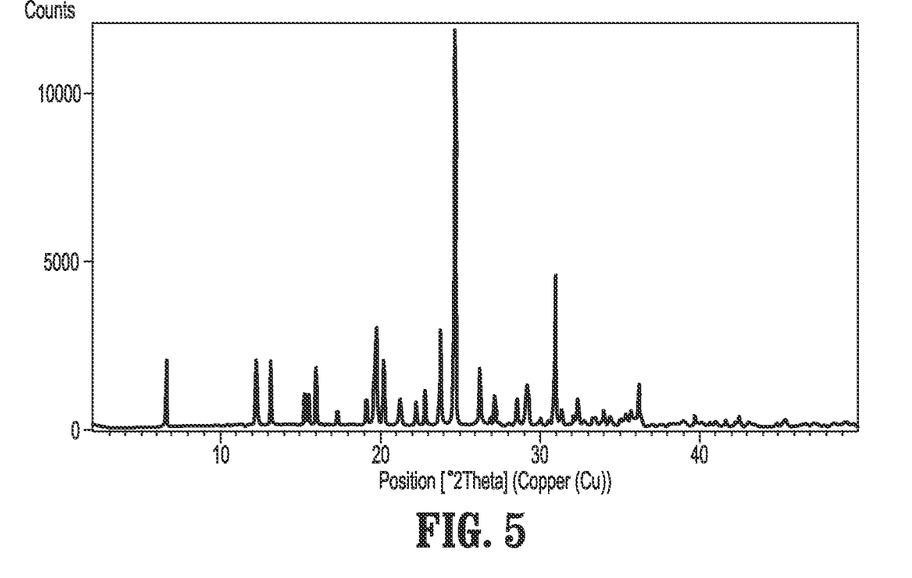
FIG. 5 is a characteristic XRPD of solriamfetol hydrochloride as obtained in Example 20.

In one embodiment, the present invention provides a crystalline solriamfetol HCl characterized by an X-ray powder diffraction (XRPD) spectrum having peak reflections at about 6.58, 12.27, 13.18, 19.81, 24.66, 30.98±0.2 degrees 2 theta which is substantially in accordance with FIG. 5.

Figure 6:
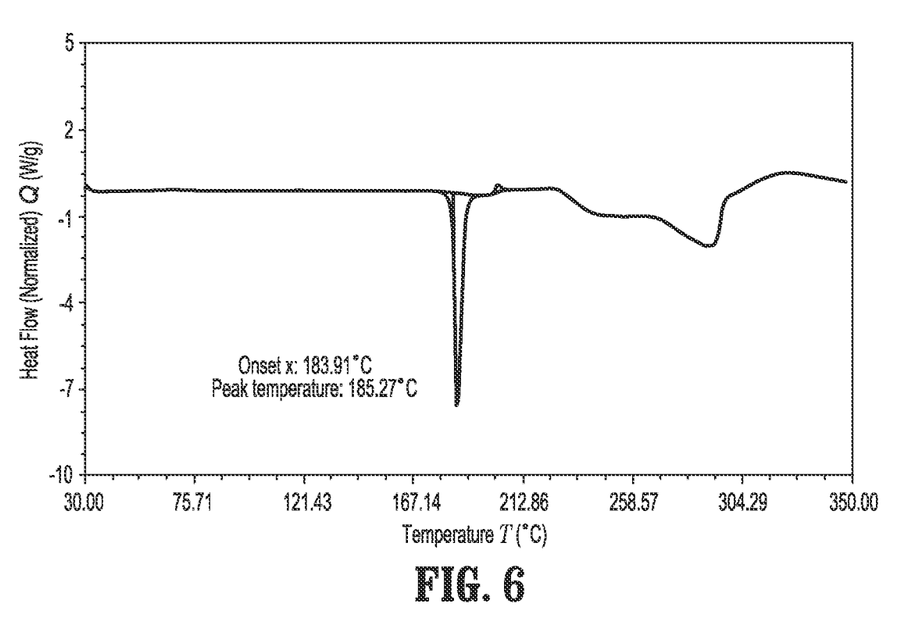
FIG. 6 is a DSC thermogram of solriamfetol hydrochloride as obtained in Example 20.

In one embodiment, the present invention provides a crystalline solriamfetol HCl characterized by DSC thermogram having endothermic peak at about 183.91±2° C. and about 185.27±2° C. which is substantially in accordance with FIG. 6.

Figure 7:
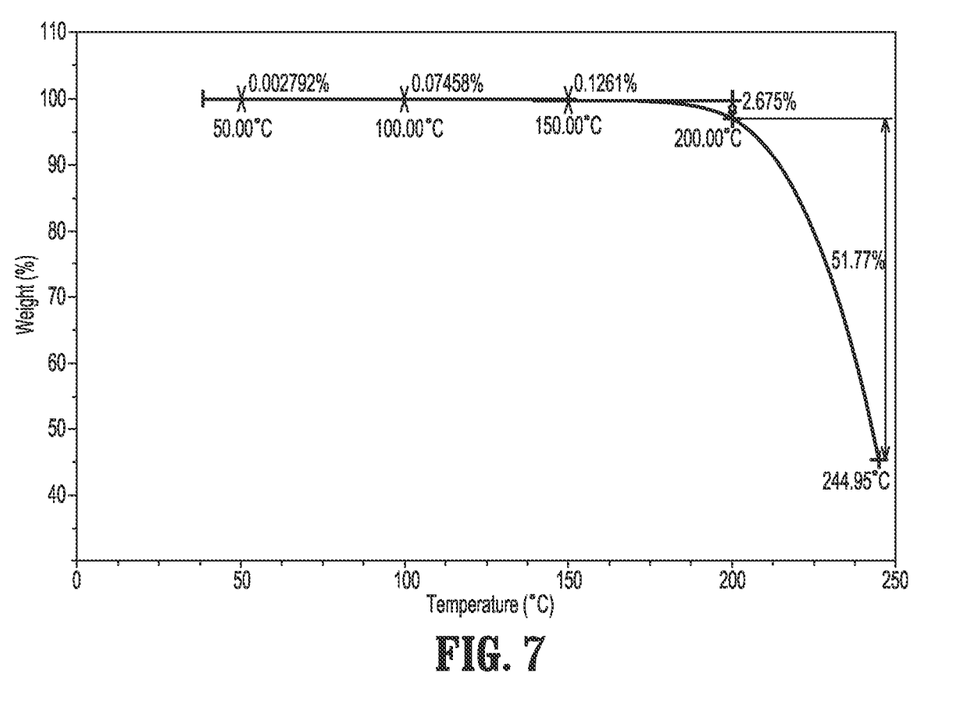
FIG. 7 is a TGA thermogram of solriamfetol hydrochloride as obtained in Example 20.

In one embodiment, present invention provides crystalline solriamfetol HCl characterized by TGA thermogram, showing weight loss of about less than 0.1 weight % up to 100° C. determined over the temperature range of 0° C. to 350° C. and heating rate 10° C./min which is substantially in accordance with FIG. 7.

In one embodiment, present invention provides crystalline solriamfetol hydrochloride showing water content less than 0.5% by KF.

In one embodiment, the present invention provides solriamfetol hydrochloride, having $D_{10}$ particle size of less than about 50 microns, preferably less than about 20 microns, more preferably less than about 10 microns.

In one embodiment, the present invention provides solriamfetol hydrochloride, having $D_{50}$ particle size of less than about 150 microns, preferably less than about 130 microns, more preferably less than about 115 microns.

In one embodiment, the present invention provides solriamfetol hydrochloride, having $D_{90}$ particle size of less than about 300 microns, preferably less than about 250 microns, more preferably less than about 225 microns.

The particle size disclosed here can be obtained by, for example, any milling, grinding, micronizing or other particle size reduction method known in the art to bring the solid state solriamfetol or hydrochloride or solvate thereof into any of the foregoing desired particle size range.

In one embodiment, the present invention provides a process for the preparation of D-phenyl alanine methyl ester HCl of formula IV, Formula IV the process comprising reacting D-phenyl alanine with thionyl chloride in presence of solvent or mixture of solvents to form formula IV.

In one embodiment, formula IV may be purified or crystallized from solvent or mixture of solvents.

In one embodiment, the present invention provides a process for the preparation of (2R)-2-amino-3-phenylpropan-1-ol of formula III, Formula III the process comprising reacting formula IV with reducing agent in the presence of a base and suitable organic solvent or mixture of organic solvents.

In one embodiment, formula III may be purified or crystallized from solvent or mixture of solvents.

In one embodiment, the present invention provides a process for the preparation of solriamfetol of formula I, Formula I the process comprising reacting formula III with an alkali cyanate or alkaline earth cyanate and an acid in presence an organic solvents.

The present invention provides solriamfetol hydrochloride, obtained by the above processes, as characterized and analyzed by following techniques:

A. X-ray powder diffraction profiles were obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator; Scanning Mode; Active length (2Theta)=2.122°; generator 45 KV; tube current 40 mAmp. The samples were scanned in the full 2θ range of 2–50° with a "time-per-step" optimized to 50 sec.

B. DSC (TA 250): Temperature range is "30° C. to 350° C." and heating rate is 10° C./minute.

C. Thermo Gravimetric Analyzer: TGA Q500 V6.5. Thermogram was recorded at 30-350° C. at the rate of 10° C./min.

D. Karl Fischer: The water content was calculated by the following formula:

water content(%)=Burette reading×KF Factor/Weight of sample in mg×100

The examples that follow are provided to enable one skilled in the art to practice the invention and are merely illustrative of the invention. The examples should not be read as limiting the scope of the invention as defined in the features and advantages.

EXAMPLES

Example 1: Preparation of (2R)-2-amino-3-phenylpropan-1-ol

To a stirred solution of D-phenylalanine methyl ester hydrochloride (100 gm) in methylene dichloride (500 ml) and water (300 ml), sodium carbonate (50 gm) added in one lot at about 25-30° C. The reaction mixture was stirred for about 30 minutes and organic layer was separated and collected in clean and dry container. The aqueous layer was extracted with methylene dichloride. The combined organic layer was washed with water and dried over $Na_2SO_4$. The organic layer was evaporated under vacuum to give D-phenylalanine methyl ester as an oil (79 gm) which was taken in methanol and reaction mixture was cooled to 0-5° C. Sodium borohydride (35.304 gm) was added to reaction mixture lot wise by maintaining temperature between 0-10° C. in about 1 hour. The ice-bath was removed and reaction mixture was stirred until D-phenylalanine methyl ester was no longer detected by TLC. After completion of reaction, solvent was evaporated and thick solid was dissolved in water. The aqueous layer was extracted three times with methylene dichloride. The product containing methylene dichloride was concentrated and n-heptane (600 ml) was added. The slurry was stirred for about 2 hour and the precipitated solid was collected by filtration. The solid was dried under vacuum to form titled compound as a white solid. Yield: 57 gm, 81%.

Example 2: Preparation of Crystalline (2R)-2-amino-3-phenylpropyl Carbamate (Solriamfetol)

In a dry round bottom flask dichloromethane (224 mL) was charged followed by addition of (2R)-2-amino-3-phenylpropan-1-ol (28 g) and sodium cyanate (23.59 g). The reaction mixture was cooled to about 0-5° C. and methane sulfonic acid (62.28 g) was slowly added to the reaction mass. After completion of the addition of methane sulfonic acid, temperature of the reaction mass was raised to about 20-30° C. and stirred for about 3 hours. After completion of the reaction, the reaction mass cooled to about 0-5° C. and 20% aq. sodium hydroxide solution was added at temperature below 5° C. The aqueous and organic layers were separated and the aqueous phase was extracted with dichloromethane. The combined organic phase was washed with water and brine and dried over sodium sulfate overnight followed by filtration. The filtrate was concentrated under vacuum to obtain 29.5 g solriamfetol as an oil. The obtained oil was taken in n-heptane (300 ml) and stirred for about 5 hours at 0-10° C. The precipitated solid was filtered and dried under vacuum at about 20-30° C. to form 27 gm of titled compound.

Example 3: Preparation of Crystalline Solriamfetol Hydrochloride

Solriramfetol (1 gm) was dissolved in dichloromethane (5 ml) in round bottom flask. The reaction mass cooled to about 0-5° C. and ethyl acetate hydrochloride (3 ml) was added at about 0-5° C. The reaction mixture was stirred for about 1 hour, a white precipitated formed. The obtained precipitate was filtered and dried in vacuum at about 50° C. to form 1 gm of titled compound.

Example 4: Preparation of Solriamfetol

A solution of methane sulfonic acid (88.98 gm) in 80 ml dichloromethane was charged slowly to a solution of D-phenylalaninol (40 gm) and sodium cyanate (33.7 gm) in 320 ml dichloromethane at about 0-5° C. and the reaction mass was stirred for about 3 hours. The progress of reaction was monitored by TLC till completion of the reaction. After completion of reaction, water was added and pH of the reaction mixture was adjusted in between 10 to 12 using 20% sodium hydroxide solution. The mixture was transfer to separator and organic layer separated. Aqueous layer was extracted with dichloromethane. Combined organic layer was washed with brine solution and dried over sodium sulphate. Organic layer was concentrated in vacuum to get an oil which was stirred in 300 ml n-heptane at 0-5° C. for about 15 minutes then temperature was raised to 20-30° C. and stirred for about 2 hour. The precipitated solid was filtered and dried under vacuum at about 35-40° C. for about 12 hours to form titled compound as a solid. Yield: 43 gm, 71%; HPLC chemical purity: 92%.

Example 5: Preparation of Solriamfetol Dibenzoyl-D-Tartaric Acid

A solution of solriamfetol dibenzoyl-D-tartaric acid (11.12 gm) in 50 ml dichloromethane was added to a stirred solution of solriamfetol free base (6.2 gm) from example 4 in 50 ml dichloromethane in about 20 minutes. The thick slurry of reaction mass was stirred for about two hour at 25-30° C. The precipitated solid was filtered and dried under vacuum at about 50-60° C. for about 12 hours to form 16.5 gm of titled compound (solriamfetol DBTA salt) as a white solid. Yield: 16.5 gm, 92%; HPLC chemical purity: 87.60%

Example 6: Purification of Solriamfetol Dibenzoyl-D-Tartaric Acid

A suspension of solriamfetol dibenzoyl-D-tartaric acid salt (5 gm) in 25 ml isopropyl alcohol containing 10% water was heated to reflux to get a clear solution and stirred for about 30 minutes the reaction mass was cooled gradually to room temperature and stirred for about 2 hour. The solid was filtered and dried under vacuum at 50-60° C. to form 2.2 gm of titled compound. HPLC chemical purity: 99.16%. $^1$H NMR, 400 MHZ, DMSO, ppm: 2.65-2.71 (t, 1H), 2.88 (m, 1H), 3.39 (q, 1H), 3.72-3.86 (m, 4H), 5.69 (s, 1H), 6.61 (br s, 2H), 7.16-7.25 (m, 5H), 7.44-7.48 (m, 5H), 7.60-8.00 (m, 5H).

Example 7: Preparation of Solriamfetol HCl 5 ml ethyl acetate hydrochloride (10-12%) was added slowly to a suspension of 1 gm solriamfetol dibenzoyl-D-tartaric acid salt obtained from example 6 in 5 ml ethyl acetate and the reaction mixture was stirred for about 2 hours at room temperature. The precipitated solid was filtered and dried under vacuum at about 50-60° C. for about 12 hours to form 1 gm of titled compound. HPLC chemical purity: 99.47%;

HPLC chiral purity greater than 99%.

Example 8: Preparation of Solriamfetol Di-p-Toluoyl-D-Tartaric Acid

To a stirred solution of solriamfetol free base (5 gm) from example 4, in 30 ml ethyl acetate was added di-p-toluoyl-d-tartaric acid salt (9.93 gm) solution in 30 ml ethyl acetate in about 20 minutes. The thick slurry of reaction mass was stirred for two hour at 25-30° C. The precipitated solid was filtered and dried under vacuum for overnight to afford 5.7 gm of titled compound as a white solid. HPLC chemical purity: 96.37%; $^1$H NMR, 400 MHZ, DMSO, ppm: 2.34 (m, 1H), 2.70-2.76 (m, 1H), 2.88-2.93 (m, 1H), 3.48-3.51 (q, 1H), 3.72-3.86 (m, 4H), 5.60 (s, 1H), 6.61 (br s, 2H), 7.16-7.31 (m, 8H), 7.84-7.86 (m, 5H).

XRD peaks of crystalline solriamfetol di-p-toluoyl-D-tartaric acid obtained are listed in Table 1

TABLE 1

| Pos. [°2Th.] | Rel. Int. [%] |
|---|---|
| 6.33 | 100.00 |
| 9.65 | 1.94 |
| 11.13 | 9.33 |
| 11.93 | 5.25 |
| 12.36 | 10.72 |
| 12.66 | 4.50 |
| 13.52 | 16.60 |
| 15.26 | 13.64 |
| 15.59 | 18.95 |
| 16.32 | 35.53 |
| 18.23 | 18.26 |
| 18.55 | 32.79 |
| 19.65 | 36.18 |
| 21.85 | 42.75 |
| 22.78 | 7.84 |
| 23.95 | 18.78 |
| 24.23 | 20.10 |
| 24.81 | 7.38 |
| 25.31 | 20.64 |
| 26.44 | 18.69 |
| 26.87 | 13.18 |
| 28.30 | 3.78 |
| 28.61 | 1.88 |
| 29.00 | 4.51 |
| 30.15 | 6.34 |
| 30.35 | 6.26 |
| 31.44 | 3.79 |
| 32.39 | 2.39 |
| 33.66 | 2.07 |
| 34.16 | 1.70 |
| 35.79 | 3.47 |
| 36.28 | 2.32 |

TABLE 1-continued

| Pos. [°2Th.] | Rel. Int. [%] |
|---|---|
| 37.57 | 2.18 |
| 38.61 | 1.64 |
| 39.87 | 0.65 |
| 41.13 | 0.81 |
| 42.84 | 1.18 |
| 43.88 | 2.24 |
| 44.44 | 2.06 |
| 46.79 | 1.95 |

DSC analysis of solriamfetol di-p-toluoyl-D-tartaric shows endothermic peaks at about 184.57° C. and 190.37° C.

TGA analysis of solriamfetol di-p-toluoyl-D-tartaric shows a weight loss of less than 1.0 weight % up to 100° C. determined over the temperature range of 0° C. to 350° C. and heating rate 10° C./min.

Example 9: Preparation of Solriamfetol HCl 5 ml ethyl acetate HCl solution (10-12%) was added slowly to a suspension of 2 gm solriamfetol di-p-toluoyl-D-tartaric acid salt obtained from example 8, in 20 ml ethyl acetate. After the complete addition mixture was stirred for about 2 hours and solid was collected by filtration. The product was washed with ethyl acetate and dried under vacuum at about 50-60° C. for about 12 hours to form 1 gm of titled compound. HPLC chemical purity: 99.52%; HPLC chiral purity greater than 99%.

Example 10: Preparation of Solriamfetol Oxalate

To a stirred solution of solriamfetol free base (8 gm) from example 4, in 30 ml ethyl acetate was added oxalic acid (5.18 gm) solution in 30 ml ethanol in about 20 minutes. The thick slurry of reaction mass was stirred for about two hour at 25-30° C. The precipitated solid was filtered and dried under vacuum for overnight to afford 8.5 gm of titled compound as a white solid. $^1$H NMR, 400 MHZ, DMSO, ppm: 2.80-2.86 (m, 1H), 2.98-3.03 (m, 1H), 3.57-3.58 (q, 1H), 3.82-4.00 (m, 4H), 6.64 (br s, 2H), 7.26-7.36 (m, 5H), 8.89 (br s, 4H). HPLC chemical purity: 97.97%.

Example 11: Preparation of Solriamfetol HCl 5 ml ethyl acetate HCl solution (10-12%) was added slowly to a suspension of 2 gm solriamfetol oxalate obtained from example 10, in 50 ml acetone. After the complete addition mixture was stirred for about 2 hours and solid was collected by filtration. The product was washed with acetone and dried under vacuum at about 50-60° C. for about 12 hours to form 1.2 gm of titled compound. HPLC chemical purity: 98.77%.

Example 12: Preparation of Solriamfetol Tartrate

To a stirred solution of solriamfetol free base (5 gm) from example 4, in 50 ml ethyl acetate was added tartaric acid (3.85 gm) solution in 50 ml ethyl acetate in about 20 minutes. The thick slurry of reaction mass was stirred for about two hour at 25-30° C. The precipitated solid was filtered and dried under vacuum for overnight to afford 7 gm of titled compound as a white solid. HPLC chemical purity: 93.27%.

Example 13: Preparation of Solriamfetol HCl 5 ml ethyl acetate HCl solution (10-12%) was added slowly to a suspension of 2 gm solriamfetol tartrate obtained from example 12, in 50 ml acetone. After the complete addition mixture was stirred for about 2 hours and solid was collected by filtration. The product was washed with acetone and dried under vacuum at about 50-60° C. for about 12 hours to form 1.1 gm of titled compound. HPLC chemical purity: 98.81%.

Example 14: Preparation of Solriamfetol Citrate

To a stirred solution of solriamfetol free base (5 gm) from example 4 in 30 ml acetone was added citric acid (4.98 gm) solution in 30 ml acetone in about 20 minutes. The thick slurry of reaction mass was stirred for about two hour at about 25-30° C. The precipitated solid was filtered and dried under vacuum for overnight to afford 9.5 gm of titled compound as a white solid. HPLC chemical purity: 98.88%.

Example 15: Preparation of (R)-2-amino-3-phenylpropan-1-ol

To a stirred solution of D-phenylalanine methyl ester hydrochloride (100 gm) in methylene dichloride (400 ml) and aqueous sodium carbonate solution was added in one lot. The reaction mixture was stirred for about 15 minutes and organic layer was separated and collected in clean and dry container. The aqueous layer was extracted with methylene dichloride (MDC). The combined organic layer was passed over $Na_2SO_4$ and transferred to clean and dry round bottom flask. Sodium borohydride (35.304 gm) was added to organic layer in one lot and methanol (200 ml) was added to the reaction mass between 20-30° C. Reaction mixture was refluxed until D-phenylalanine methyl ester was no longer detected by HPLC. After completion of reaction, sodium chloride (10%) was added to reaction mass and stirred for about 30 minutes. Organic layer was separated and aqueous layer was extracted with MDC and product containing MDC layer was passed over $Na_2SO_4$. The organic layer was evaporated under reduced pressure to obtain solid. The solid was recrystallized from ethyl acetate and the precipitated solid was collected by filtration and dried under vacuum to form titled compound as a white solid. Yield: 50 gm, 71%; HPLC chemical purity: 99.89%.

Example 16: Preparation of Solriamfetol Dibenzoyl-D-Tartaric Acid

Methane sulfonic acid (222.40 gm) was charged slowly to a solution of (R)-2-amino-3-pheylpropan-1-ol (100 gm) and sodium cyanate (120.36 gm) in MDC (2000 ml) at about 0° C. to about 10° C. The progress of reaction was monitored by HPLC till completion of the reaction. After completion of reaction, sodium hydroxide (10%) solution was added to the reaction mass. The reaction mass was filtered through hyflow bed, organic layer was separated and aqueous layer was extracted with MDC. Combined organic layer was washed with brine solution and dibenzoyl-D-tartaric acid (118.46 gm) was added in above organic layer. The reaction mass was stirred for about 3 hours. The precipitated solid was filtered, dried under vacuum at about 50-60° C. for about 12 hours form titled compound. Yield: 220 gm; HPLC chemical purity: 96%.

Example 17: Purification of Solriamfetol Dibenzoyl-D-Tartaric Acid

Solriamfetol dibenzoyl-D-tartaric acid (200 gm) was refluxed in 5% aqueous methanol solution (1000 ml) and the suspension was stirred for about 30 minutes at reflux temperature and cooled to room temperature gradually. The thick slurry of reaction mass was stirred for about one hour at about 10-15° C. and precipitated solid was filtered and suck dried for about 30 minutes. The wet material further purified using 5% aqueous methanol to form titled compound. HPLC chemical purity: 99.63%.

XRD peaks of crystalline solriamfetol dibenzoyl-D-tartaric acid obtained are listed in Table 2

TABLE 2

| Pos. [°2Th.] | Rel. Int. [%] |
|---|---|
| 6.68 | 100.00 |
| 7.18 | 2.29 |
| 9.80 | 1.34 |
| 11.36 | 7.96 |
| 11.87 | 7.63 |
| 12.33 | 3.48 |
| 13.33 | 5.26 |
| 13.60 | 5.01 |
| 14.25 | 1.41 |
| 15.53 | 15.38 |
| 16.21 | 15.55 |
| 16.43 | 6.54 |
| 17.06 | 2.27 |
| 18.08 | 9.21 |
| 18.42 | 7.58 |
| 18.73 | 16.90 |
| 20.12 | 36.07 |
| 20.98 | 0.67 |
| 22.07 | 4.52 |
| 22.50 | 11.25 |
| 22.80 | 5.66 |
| 23.81 | 4.24 |
| 24.07 | 5.64 |
| 24.93 | 11.28 |
| 25.20 | 10.33 |
| 25.75 | 11.02 |
| 26.31 | 3.33 |
| 27.34 | 16.20 |
| 27.91 | 7.13 |
| 28.57 | 2.22 |
| 29.82 | 1.50 |
| 30.91 | 3.38 |
| 31.90 | 0.40 |
| 32.57 | 0.99 |
| 33.83 | 0.81 |
| 34.82 | 1.54 |
| 36.56 | 1.58 |
| 37.43 | 1.68 |
| 38.62 | 0.73 |
| 39.85 | 0.83 |
| 40.64 | 1.12 |
| 41.52 | 0.80 |
| 42.57 | 0.90 |
| 43.36 | 1.21 |
| 44.41 | 1.20 |
| 45.19 | 0.96 |
| 45.95 | 0.91 |
| 48.61 | 1.10 |

DSC analysis of solriamfetol dibenzoyl-D-tartaric acid shows endothermic peaks at about 177.60° C. and 181.41° C.

TGA analysis of solriamfetol dibenzoyl-D-tartaric acid shows a weight loss of less than 0.5 weight % up to 100° C. determined over the temperature range of 0° C. to 350° C. and heating rate 10° C./min

Example 18: Purification of Solriamfetol Dibenzoyl-D-Tartaric Acid

Solriamfetol dibenzoyl-D-tartaric acid (200 gm) was refluxed in 5% aqueous ethanol solution (1000 ml) and suspension was stirred for about 30 minutes at reflux temperature and cooled to room temperature gradually. The thick slurry of reaction mass was stirred for about one hour at about 10-15° C. and precipitated solid was filtered and suck dried for about 30 minutes. The wet material further purified using 5% aqueous ethanol to form titled compound. HPLC chemical purity: 98.35%.

Example 19: Preparation of Solriamfetol Hydrochloride

Solriamfetol dibenzoyl-D-tartaric acid obtained from example 17 was charged in ethyl acetate (800 ml) and water (400 ml). The reaction mass was cooled below 20° C. and aqueous sodium hydroxide solution was added slowly to get clear solution. The mixture was transfer to separator and organic layer was separated. Aqueous layer was extracted with ethyl acetate (2 time). Combined organic layer was washed with purified water and filtered through hyflow bed and concentrated under vacuum to get an oil (80 gm). Obtained oily mass was dissolved in isopropanol (240 ml) and IPA-HCl (117 ml) was added slowly below 10° C. The precipitated solid was stirred for 2 about hour, filtered, dried under vacuum at about 50-60° C. for about 12 hours to form titled compound as white solid. Yield: 90 gm; HPLC chemical purity: 99.96%; chiral purity: 100%.

Example 20: Purification of Solriamfetol Hydrochloride

Solriamfetol Hydrochloride (100 gm) was dissolved in methanol (500 ml) and stirred for about 30 minutes to get clear solution, filtered through suitable filter to remove foreign particle and distilled under vacuum. The obtained solid was slurried in ethyl acetate (500 ml), filtered and dried under vacuum at about 65-70° C. for about 12 hours to form titled compound. Melting point: 177-179° C.; Yield: 95 gm white solid; HPLC chemical purity: 99.96%; chiral purity 100%. XRD peaks of crystalline solriamfetol hydrochloride obtained are listed in Table 3

TABLE 3

| Pos. [°2Th.] | Rel. Int. [%] |
|---|---|
| 6.58 | 17.5 |
| 12.27 | 16.27 |
| 13.17 | 16.85 |
| 15.33 | 8.02 |
| 15.54 | 7.57 |
| 16.04 | 14.91 |
| 17.32 | 3.89 |
| 19.19 | 6.82 |
| 19.64 | 13.03 |
| 19.81 | 25.41 |
| 20.24 | 16.96 |
| 21.20 | 5.58 |
| 21.29 | 6.79 |
| 22.26 | 5.63 |
| 22.84 | 8.83 |
| 23.72 | 24.52 |
| 24.66 | 100.00 |
| 26.21 | 14.57 |
| 26.91 | 2.41 |
| 27.17 | 7.69 |

TABLE 3-continued

| Pos. [°2Th.] | Rel. Int. [%] |
|---|---|
| 28.58 | 6.70 |
| 29.20 | 10.39 |
| 29.28 | 9.24 |
| 30.01 | 1.92 |
| 30.55 | 1.36 |
| 30.98 | 38.81 |
| 31.37 | 3.98 |
| 32.11 | 2.54 |
| 32.41 | 6.70 |
| 32.78 | 1.36 |
| 33.35 | 2.02 |
| 34.03 | 4.08 |
| 34.45 | 2.16 |
| 35.07 | 2.30 |
| 35.39 | 3.16 |
| 35.71 | 4.15 |
| 35.95 | 3.07 |
| 36.19 | 10.38 |
| 37.61 | 0.69 |
| 39.05 | 1.83 |
| 39.70 | 2.82 |
| 40.10 | 0.83 |
| 40.99 | 1.71 |
| 41.62 | 1.42 |
| 42.21 | 1.02 |
| 42.46 | 2.81 |
| 43.09 | 1.45 |
| 44.18 | 0.71 |
| 44.86 | 1.16 |
| 45.40 | 1.92 |

DSC analysis of solriamfetol hydrochloride shows endothermic peaks at about 183.91° C. and 185.27° C.

TGA analysis of solriamfetol hydrochloride shows a weight loss of less than 0.1 weight % up to 100° C. determined over the temperature range of 0° C. to 350° C. and heating rate 10° C./min.

Particle size: d(10) 5.109; d(50) 101.52; d(90) 213.34

Comparative Example 1: Preparation of Solriamfetol Hydrochloride

10% ethyl acetate hydrochloride (20 ml) was added slowly to a solution of solriamfetol free base (10 gm) from example 4 in 50 ml ethyl acetate and stirred for about 2 hours at about 25-30° C. The precipitated solid was filtered and was washed with ethyl acetate. The solid was dried under vacuum at about 50-60° C. for about 12 hours to afford titled compound as white solid. Yield: 11 gm, 73%; HPLC chemical purity: 95.11%.

Comparative Example 2: Purification of Solriamfetol Hydrochloride

A suspension of solriamfetol hydrochloride (2 gm) in 20 ml of ethyl acetate was heated to reflux and stirred for about 30 minutes the reaction mass was cooled gradually to room temperature and further stirred for about 2 hours. The solid was filtered and dried under vacuum at about 50-60° C. to yield 1.5 gm of titled compound. HPLC chemical purity: 97%; $^1$H NMR, 400 MHZ, DMSO, ppm: 2.50-2.51 (t, 1H), 2.84 (m, 1H), 3.09 (q, 1H), 3.84-4.01 (m, 4H), 6.62 (s, 2H), 7.24-7.35 (m, 5H), 8.40 (br s, 3H).

The above process was repeated using below listed solvents instead of ethyl acetate.

| Purification solvent | HPLC Chemical Purity |
|---|---|
| Acetonitrile | 87.09% |
| Methyl tertiary butyl ether | 93.88% |
| Ethanol | 94.12% |
| Acetic acid | 97.59% |

We claim:

1. A process for the preparation of R-solriamfetol HCl of Formula Ia,

Formula Ia the process comprising:

(a) reacting solriamfetol of Formula I,

Formula I with an acid to form solriamfetol acid addition salt of Formula II;

Formula II (b) optionally purifying the solriamfetol acid addition salt of Formula II;

(c) converting the solriamfetol acid addition salt of Formula II to solriamfetol HCl of Formula Ia; and (d) optionally purifying the solriamfetol HCl of Formula Ia.

2. The process of claim 1, wherein the chemical purity of R-solriamfetol HCl of Formula Ia is at least 98%, as determined by HPLC.

3. The process of claim 1, wherein the acid is selected from the group consisting of an organic acid and an optically active acid.

4. The process of claim 3, wherein the organic acid is selected from the group consisting of formic acid, acetic acid, citric acid, tartaric acid, benzoic acid, lactic acid, oxalic acid, malic acid, fumaric acid, succinic acid, gluconic acid, pamoic acid, methanesulfonic acid, and benzenesulfonic acid.

5. The process of claim 3, wherein the optically active acid is selected from the group consisting of (+)-dibenzoyl-D-tartaric acid, (−)-dibenzoyl-L-tartaric acid, (+)-di-p-toluoyl-D-tartaric acid, (−)-d-p-toluoyl-L-tartaric acid, S-(+) mandelic acid, R-(−) mandelic acid, L-(+) tartaric acid, D-(−) tartaric acid, L-malic acid, D-malic acid, D-maleic acid, (1R)-(−)-camphor sulfonic acid, (1S)-(+)-camphor sulfonic acid, L(−)-pyroglutamic acid, L(+)-pyroglutamic acid, and (−)-lactic acid.

6. The process of claim 1, wherein in step (c) the solriamfetol acid addition salt of Formula II is treated with an HCl source in an organic solvent to form the R-solriamfetol HCl of Formula Ia.

7. The process of claim 6, wherein the organic solvent is selected from the group consisting of an ester, an ether, a ketone and an alcohol.

8. The process of claim 1, wherein the solriamfetol acid addition salt of Formula II is a solriamfetol dibenzoyl-D-tartaric acid salt of Formula IIa Formula IIa 9. Solriamfetol dibenzoyl-D-tartaric acid salt of Formula IIa,

Formula IIa characterized by an ¹H NMR having peaks at 2.65-2.71, 2.88, 3.39, 3.72-3.86, 5.69, 6.61, 7.16-7.25, 7.44-7.48, and 7.60-8.00, measured at 400 MHz in DMSO $d_6$.

10. A process for preparing solriamfetol dibenzoyl-D-tartaric acid salt of Formula IIa, Formula IIa comprising reacting solriamfetol of Formula I, Formula I with dibenzoyl-D-tartaric acid.

* * * * *